United States Patent [19]
Johnson et al.

[11] Patent Number: 6,136,006
[45] Date of Patent: *Oct. 24, 2000

[54] APPARATUS FOR DELIVER AND DEPLOYMENT OF A STENT

[75] Inventors: Liann M. Johnson, Golden Valley; Richard J. Thompson, Watertown, both of Minn.; John A. Scholl, Danville, Calif.

[73] Assignee: Boston Scientific Corporation, Natick, Mass.

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 09/123,389

[22] Filed: Jul. 27, 1998

Related U.S. Application Data

[63] Continuation of application No. 08/843,750, Apr. 21, 1997, Pat. No. 5,817,102, and a division of application No. 08/614,917, Mar. 13, 1996, Pat. No. 5,876,448, and a continuation of application No. 08/221,459, Apr. 1, 1994, abandoned, and a continuation of application No. 07/880,435, May 8, 1992, abandoned.

[51] Int. Cl.$^7$ ..................................................... A61B 17/00

[52] U.S. Cl. .......................................... 606/108; 623/1.12

[58] Field of Search .................................... 606/108, 191, 606/198; 623/1.11, 1.12, 1.23; 604/220

[56] References Cited

U.S. PATENT DOCUMENTS

| | | |
|---|---|---|
| 3,868,956 | 3/1975 | Alfidi et al. . |
| 4,553,545 | 11/1985 | Maass et al. . |
| 4,572,186 | 2/1986 | Gould et al. . |

(List continued on next page.)

FOREIGN PATENT DOCUMENTS

| | | |
|---|---|---|
| AU-B-58712 | 11/1991 | Australia . |
| AU-B-32185 | 8/1993 | Australia . |
| 1205743 | 9/1970 | European Pat. Off. . |
| 0 183 372 | 4/1986 | European Pat. Off. . |
| 0 408 245 | 1/1991 | European Pat. Off. . |
| WO 87/04935 | 2/1987 | WIPO . |
| WO 93/17636 | 9/1993 | WIPO . |

OTHER PUBLICATIONS

*Endoscopy*, No. 3. vol. 22 (May 1990) New Techniques, "Self–Expanding Mesh Stent for Esophageal Cancer Stenosis", W. Domschke et al, pp. 134–136.

*Radiology*, vol. 180, No. 2, (Aug. 1991), "Esophagogastric Neoplasms:Palliatton with a Modified Geanturco Stent", Song et al, pp. 349–354.

(List continued on next page.)

*Primary Examiner*—Michael H. Thaler
*Attorney, Agent, or Firm*—Westman, Champlin & Kelly, P.A.

[57] ABSTRACT

A radially self-expanding stent particularly suited for treating esophageal strictures, includes a medial region and proximal and distal cuffs having diameters greater than the medial region diameter when the stent is in the relaxed state. A silicone coating circumscribes the medial region, but the cuffs are not coated and retain their open weave construction. As a result, the cuffs remain particularly well suited to immediately contact esophageal wall tissue and resist stent migration, while the silicone coated medial region provides a barrier to tumor ingrowth, and has an enhanced radial restoring force to maintain an open passageway in the esophagus. A deployment device for the stent includes an interior catheter surrounded by the stent and having an esophageal dilation feature, along with an exterior catheter that radially compresses the stent. A low durometer sleeve, fixed to the interior tube and in surface engagement with the compressed stent, tends to fix the axial position of the stent relative to the interior catheter whenever the exterior catheter is moved axially relative to the inner catheter. Consequently, precision in stent placement and the ability to recapture a partially deployed stent are enhanced.

16 Claims, 5 Drawing Sheets

U.S. PATENT DOCUMENTS

| | | |
|---|---|---|
| 4,580,468 | 4/1986 | Gianturco . |
| 4,649,922 | 3/1987 | Wiktor . |
| 4,655,771 | 4/1987 | Wallsten . |
| 4,681,110 | 7/1987 | Wiktor . |
| 4,699,611 | 10/1987 | Bowden . |
| 4,723,549 | 2/1988 | Wholey et al. . |
| 4,732,152 | 3/1988 | Wallsten et al. . |
| 4,733,665 | 3/1988 | Palmaz . |
| 4,768,507 | 9/1988 | Fischell et al. . |
| 4,793,348 | 12/1988 | Palmaz . |
| 4,794,928 | 1/1989 | Kletschka . |
| 4,800,882 | 1/1989 | Gianturco . |
| 4,830,003 | 5/1989 | Wolff et al. . |
| 4,848,343 | 7/1989 | Wallsten et al. . |
| 4,856,516 | 8/1989 | Hillstead . |
| 4,877,030 | 10/1989 | Beck et al. . |
| 4,886,062 | 12/1989 | Wiktor . |
| 4,921,484 | 5/1990 | Hillstead . |
| 4,955,899 | 9/1990 | Della Corna et al. . |
| 4,973,301 | 11/1990 | Nissenkorn . |
| 5,015,253 | 5/1991 | MacGregor . |
| 5,026,377 | 6/1991 | Burton et al. . |
| 5,064,435 | 11/1991 | Porter . |
| 5,071,407 | 12/1991 | Termin et al. . |
| 5,089,006 | 2/1992 | Stiles . |
| 5,108,416 | 4/1992 | Ryan et al. . |
| 5,112,900 | 5/1992 | Buddenhagen et al. . |
| 5,123,917 | 6/1992 | Lee . |
| 5,158,548 | 10/1992 | Lau et al. . |
| 5,282,823 | 2/1994 | Schwartz et al. . |
| 5,316,023 | 5/1994 | Palmaz . |
| 5,330,500 | 7/1994 | Song . |
| 5,360,443 | 11/1994 | Barone et al. . |
| 5,405,377 | 4/1995 | Cragg . |

OTHER PUBLICATIONS

*Endoscopy*, "A New Coatred Self–Expanding Metal for Malignant Esophageal Strictures", Jul./Aug. 1992 issue, Fleischer and Ball–Henry, vol. 38, No. 4, pp. 494–496.

*Endoscopy*, "Silicone–Covered Expandable Metallic Stents in the Esophagus: An Experimental Study", 1992, vol. 24, pp. 416–420.

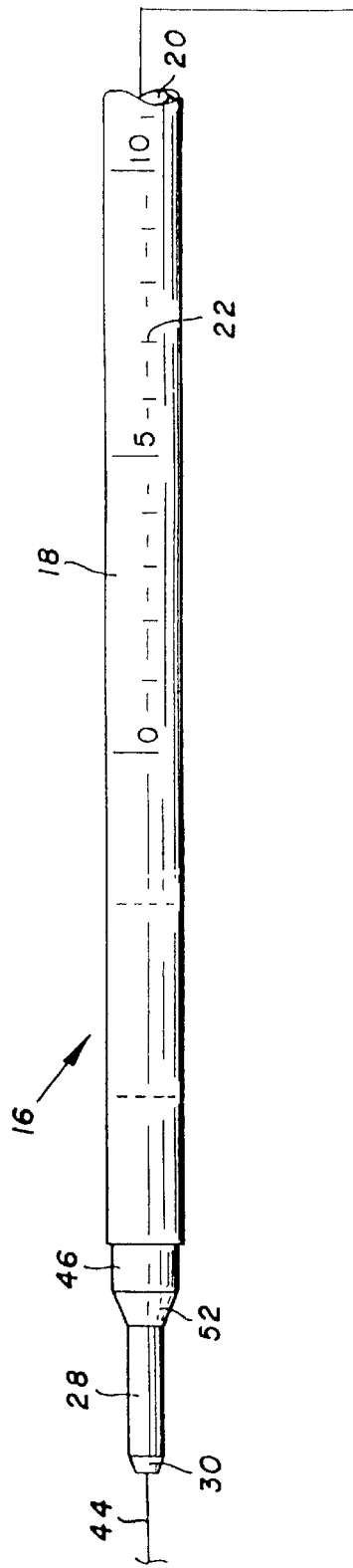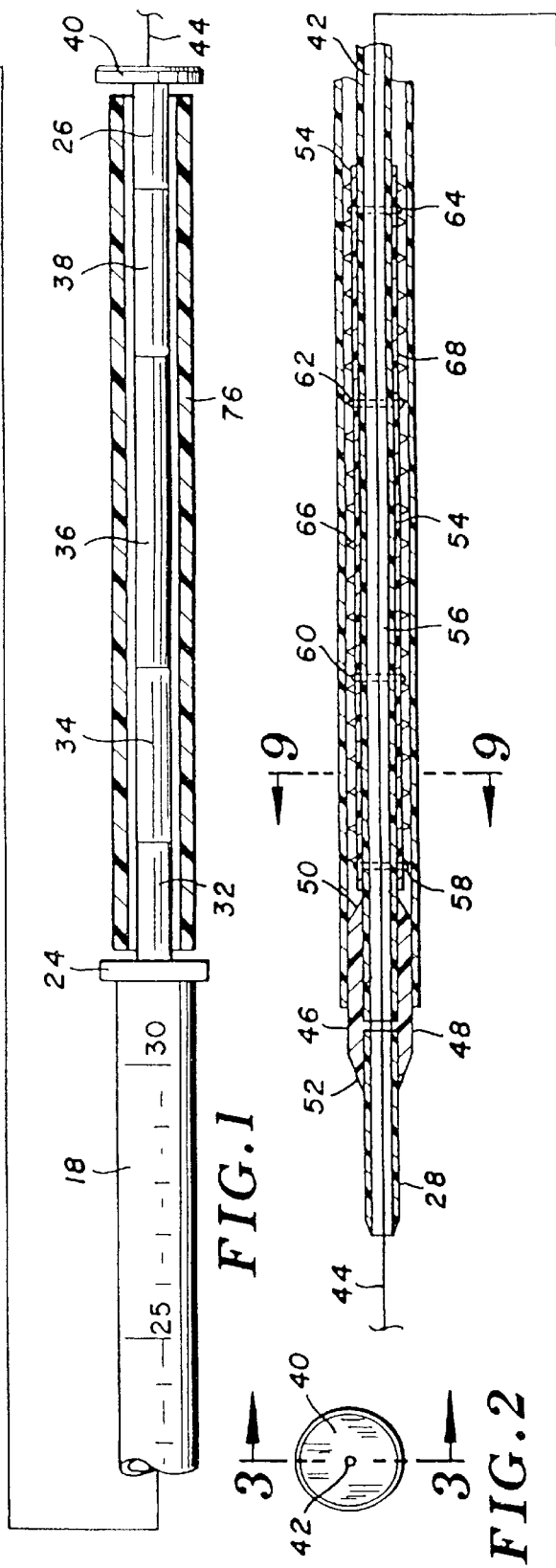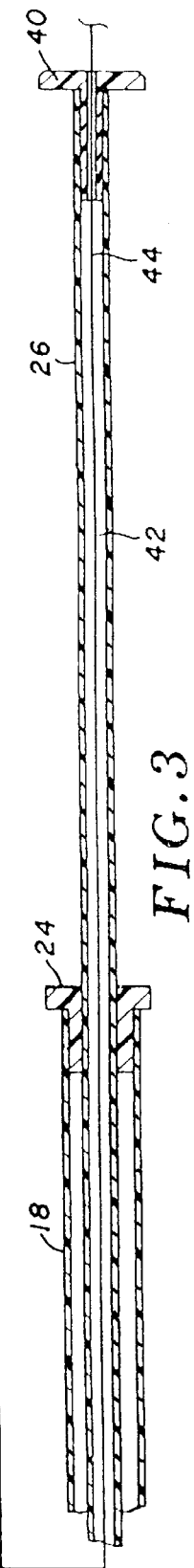
FIG.1
FIG.2
FIG.3

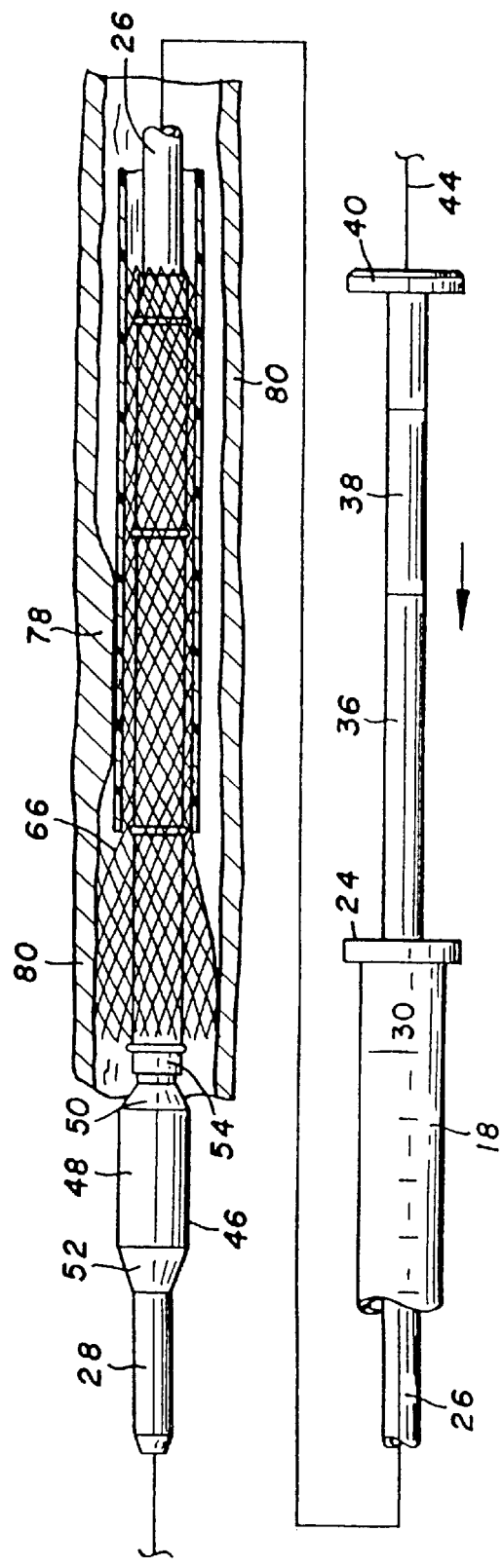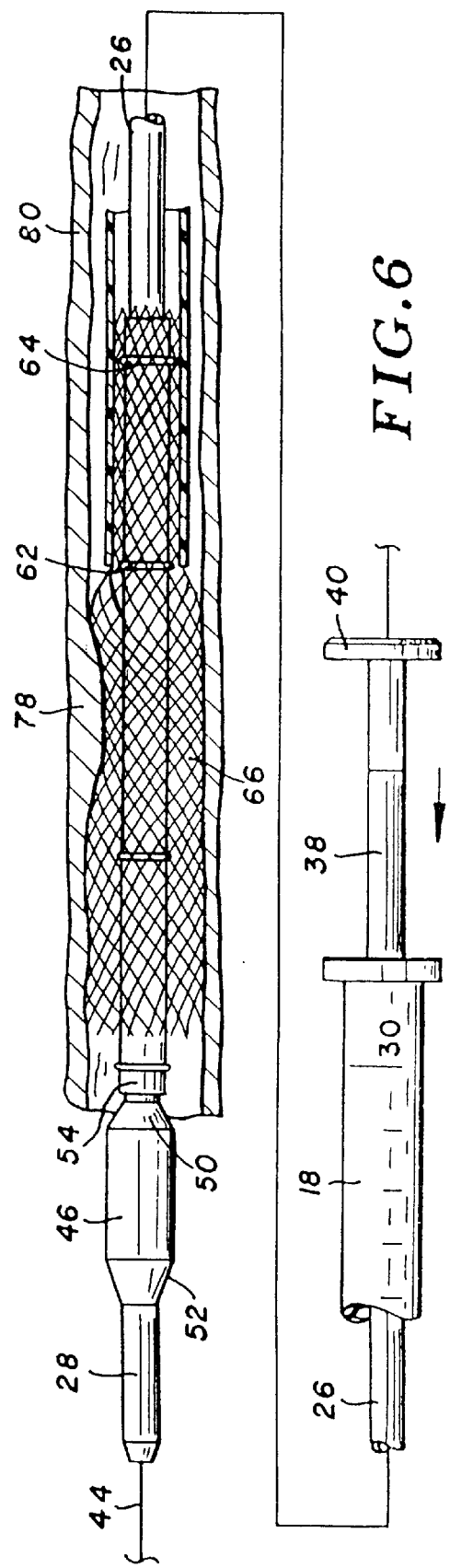

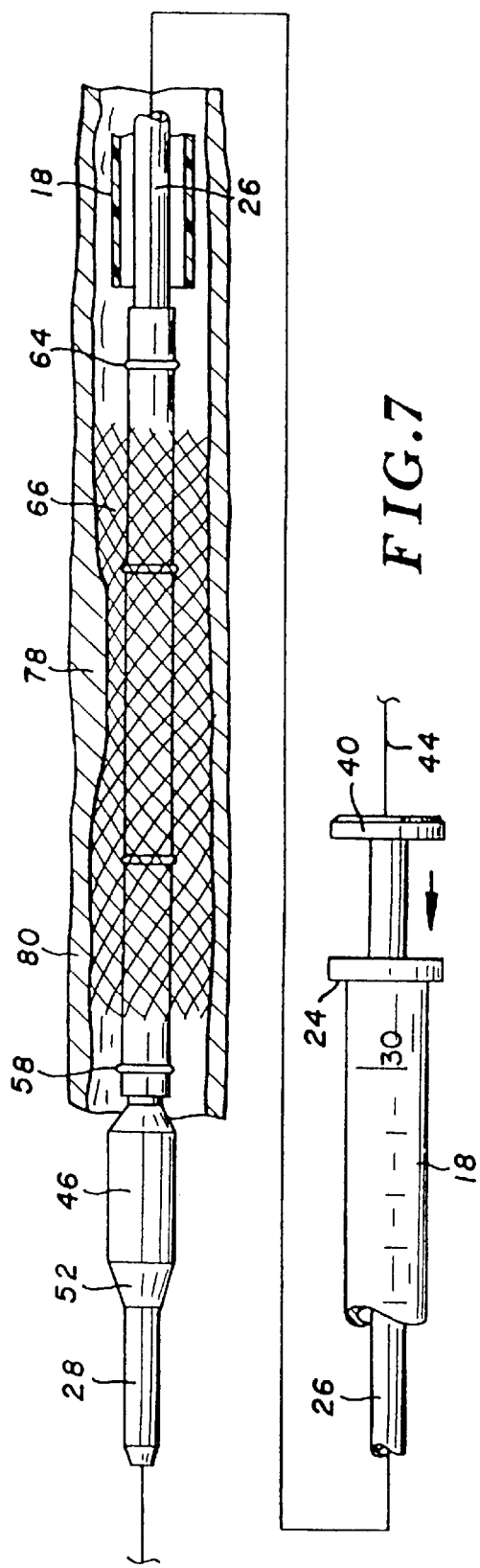
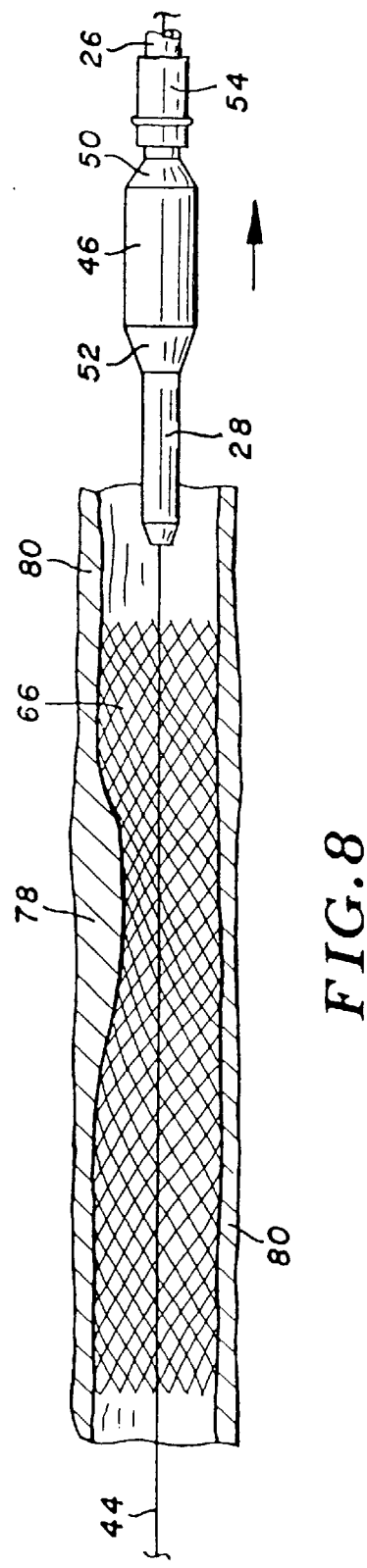
FIG. 7
FIG. 8

6,136,006

APPARATUS FOR DELIVER AND DEPLOYMENT OF A STENT

This is a continuation of application Ser. No. 08/843,750, filed on Apr. 21, 1997 now U.S. Pat. No. 5,817,102 as a divisional application of prior application Ser. No. 08/614,917, filed Mar. 13, 1996 now U.S. Pat. No. 5,876,448 as a continuing application of prior application Ser. No. 08/221,459 filed Apr. 1, 1994 now abandoned as a continuation of original application Ser. No. 07/880,435, entitled "Esophageal Stent", filed May 8, 1992 now abandoned.

BACKGROUND OF THE INVENTION

The present invention relates to body implantable treatment devices, and more particularly to stents and other prostheses intended for fixation in body lumens especially including the esophagus.

Carcinomas in the esophagus lead to progressive dysphagia, i.e. difficulty in swallowing, and the inability to swallow liquids in the most severe cases. While surgical removal is sometimes effective, the majority of patients have tumors that can not be surgically removed. Repeated dilations of the esophagus provide only temporary relief.

Difficult or refractory cases often are treated by intubation using rigid plastic prostheses, or laser therapy with an Nd:YAG laser. These techniques, while often effective, have disadvantages. Rigid plastic protheses are large, for example having a diameter of 10–12 mm and larger (25–29 mm) outer end flanges. Placement of rigid plastic stents is traumatic, and too frequently causes perforation of the esophageal wall. These protheses further are subject to migration, obstruction with food or tumor ingrowth, and late pressure necrosis.

Laser therapy is expensive, typically requiring several treatment sessions. Tumor recurrence is frequent, in the range of 30–40 percent. Submucosal tumors, and certain pulmonary and breast tumors causing dysphagia by esophageal compression, can not be treated by laser therapy.

The search for a more suitable prosthesis has lead to experiments with Gianturco stents, also known as Z-stents. U.S. Pat. No. 4,800,882 (Gianturco) describes such a device employed as an endovascular stent. Such stents for the esophagus have been constructed of 0.018 inch stainless steel wire, and provided with a silicone cover to inhibit tumor ingrowth. It was found necessary, however, to provide a distal silicone bumper to prevent trauma to the esophageal mucosa.

Self-expanding mesh stents also have been considered for use as esophageal prostheses. U.S. Pat. No. 4,655,771 (Wallsten) discloses a mesh stent as a flexible tubular braided structure formed of helically wound thread elements. Mesh stents appear unlikely to lead to pressure necrosis of the esophageal wall. With its inherent pliability the mesh stent, as compared to a rigid plastic stent, is insertable with much less trauma to the patient. Further, the stent can mold itself to and firmly fix itself against the esophageal wall, to resist migration. However, the stent is subject to tumor ingrowth because of the spaces between adjacent filaments.

A further difficulty with self-expanding stents, concerns their accurate placement and deployment. Typically a tube surrounds the self-expanding stent and radially compresses the stent into a reduced-radius delivery configuration. With the stent positioned at a treatment site, the outer tube is axially withdrawn, permitting the stent to radially self-expand. However, the larger size of an esophageal stent (as compared to biliary and vascular applications, for example) gives rise to substantial friction at the stent/outer tubing interface. As a result, it is difficult to precisely maintain the position of the stent during deployment, and practically impossible to retract the stent after partial deployment.

Therefore, it is an object of the present invention to provide a stent delivery device including exterior tubing surrounding the stent and movable axially to release the stent for radial self-expansion without a tendency in the stent to follow the axial movement of the exterior tubing.

Another object is to provide a stent deployment device capable of retracting a radially self-expanding stent for repositioning of the stent, even though the stent has been partially deployed and is radially expanded over the majority of its axial length.

Another object is to provide a device for delivering and deploying a prostheses to a treatment site within a body lumen, with means for dilating the body lumen at the treatment site prior to stent deployment.

A further object of the invention is to provide a radially self-expanding stent including a freely radially self-expanding fixation region in combination with a barrier region to inhibit tumor ingrowth.

Yet another object is to provide an esophageal prostheses deployable with reduced trauma to the patient, having more resistance to migration, and providing a barrier to tumor ingrowth as effective as conventional rigid plastic prostheses.

To achieve these and other objects, there is provided an apparatus for deploying a radially self-expanding stent within a body lumen. The apparatus includes a stent confining means for elastically compressing a radially self-expanding stent into a delivery configuration in which the self-expanding stent has a reduced radius along its entire axial length. The apparatus includes an elongate and flexible stent delivery device having a proximal end, a distal end and a distal region near the distal end. The distal region is used in delivering the radially self-expanding stent into a body lumen, and in positioning at a treatment site within the body lumen with the stent surrounding the delivery device along the distal region. The proximal end of the delivery device remains outside of the body. An axial restraining means is disposed along the distal region of the delivery device. A control means is operably associated with the delivery device and the confining means. The control means moves the confining means axially relative to the delivery device toward and away from a confinement position in which the confining means compresses the self-expanding stent into the delivery configuration, and urges the stent into a surface engagement with the axial restraining means. The restraining means, due to the surface engagement, tends to maintain the self-expanding stent axially aligned with the deployment device as the confining means is moved axially away from the confinement position to release the stent for radial self-expansion.

Preferably the stent delivery device is an elongate and flexible length of interior tubing, with a central lumen for accommodating a guidewire. The stent confining means can be an elongate and flexible length of tubing, having a lumen for containing the interior tubing. The second (or outer) tubing surrounds the stent to confine it.

The preferred axial restraining means is a low durometer sleeve surrounding the interior tubing along the distal region. If desired, an adhesive can be applied to an exterior surface of the sleeve. Alternatively, the axial restraining means can consist of several elongate strips disposed along the distal region, with adhesive applied to radially outward surfaces of the strips, if desired.

In either event, so long as the exterior tubing surrounds the stent to radially compress the stent, it also maintains the stent in surface engagement with the sleeve or strips. As the exterior tubing is axially withdrawn to allow part of the stent to radially self-expand, the rest of the stent remains confined against the sleeve or the strips. As a result, the stent does not travel axially with the exterior tubing. Rather, the stent remains substantially fixed in the axial direction with respect to the interior tubing. This structure affords several advantages. First, the interior tubing can be used as a means to positively maintain the radially self-expanding stent in the desired axial position during deployment. The interior tubing can itself be employed as a reliable indicator of stent position, both prior to and during deployment. Further, should the need arise to retract the stent after a partial deployment, the outer tubing can be moved back into the confinement position, without tending to carry the stent along with it.

Another aspect of the present invention is a device for fixation in a body lumen. The device includes a tubular stent of open weave construction having a predetermined normal configuration. The stent is radially compressible to a reduced-radius configuration to facilitate an axial insertion of the stent into a body lumen for delivery to a treatment site within the body lumen. A continuous film is formed axially along the stent and circumscribes the stent over a barrier region of the stent. The continuous film substantially prevents growth of tissue through the stent along the barrier region. A portion of the stent is substantially free of the continuous film to provide a fixation region of the stent for positively fixing the stent within the body lumen at the treatment site. Fixation is achieved by radial expansion of the stent into a surface engagement with a tissue wall segment defining the body lumen.

The preferred stent comprises a mesh formed of braided helical strands. The fixation region can comprise a proximal cuff and a distal cuff, with the barrier region being a medial sleeve of the stent positioned between the cuffs. Also, the barrier region preferably has a diameter less than the fixation region diameter when the stent is in its normal or relaxed configuration. A preferred material for the film is silicone. When properly controlled as to thickness, the silicone film provides a gradual self-expansion. More particularly, while the fixation region self-expands virtually instantaneously upon release of the stent, the medial barrier region, upon encountering a tumor or other striction, can take up to 24 hours to achieve a substantially complete radial self-expansion against the tumor.

This feature is particularly advantageous in connection with treating esophageal strictures, where tissue at the stricture may be severely weakened, and where normal convulsions of the esophagus tend to cause stent migration. More particularly, the rapidly expanding fixation regions contact normal esophageal tissue on either side of a stricture, and are sufficiently pliable to adjust to esophageal convulsions. Meanwhile, the barrier region of the stent experiences a gradual radial expansion, thus causing minimal disruption to tissue along the stricture.

A further feature of the invention is a system for treating a stricture within a body lumen. The system includes a radially self-expanding stent, and an elongate and flexible stent delivery device having a proximal end and distal end. The device further has a distal region for delivering the radially self-expanding stent into the body lumen and positioning the stent at a treatment site within the body lumen, with the stent surrounding the delivery device along the distal region. A first elongate and flexible length of tubing, having a lumen running the length of thereof, contains the stent delivery device within the lumen. The first tubing also elastically compresses the stent into a delivery configuration in which the stent has a reduced radius along its entire axial length. The first tubing is movable proximally relative to the delivery device and the stent, to allow the stent to radially self-expand into a surface engagement with body tissue defining the lumen. A distal tip is provided at the distal end of the stent delivery device for initially dilating a stricture at the treatment site. An enlargement feature is provided near the distal end of the stent delivery device. The enlargement feature has a diameter substantially equal to an interior diameter of the first tubing. The enlargement feature further has a distal transition region that diverges proximally from the tip to a mid-portion of the enlargement feature. The transition region further dilates the stricture to facilitate a positioning of the distal region of the first tubing along the stricture.

Preferably the distal region of the delivery device has a diameter less than the diameter of the enlargement feature mid-portion, and the enlargement feature further includes proximal transition region that converges in the proximal direction from the enlargement feature mid-portion. The proximal transition region facilitates withdrawal of the delivery device after deployment of the stent.

Thus, in accordance with the present invention, a radially self-expanding stent can be positioned accurately at a desired treatment site within a body lumen, based on an accurate positioning of the interior tubing or other stent delivery means. The stent may be allowed to radially self-expand over the majority of its axial length, and yet be retracted if necessary or desired, all while its axial position with respect to the delivery tool is maintained.

IN THE DRAWINGS

For a further appreciation of the above and other features and advantages, reference is made to the following detailed description and to the drawings, in which:

FIG. 1 is a side elevational view of a stent deployment device constructed in accordance with the present invention;

FIG. 2 is an end elevation of the device;

FIG. 3 is a sectional view taken along the line 3—3 in FIG. 2;

FIGS. 5–8 are sectional views similar to FIG. 3, showing the device at several stages of deploying a radially self-expanding stent;

Figure 11:
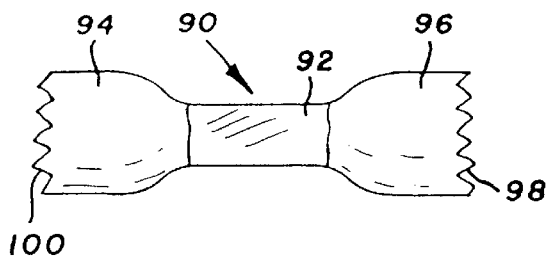
FIG. 11 is a schematic view of an esophageal prosthesis constructed in accordance with the present invention.
Figure 15:
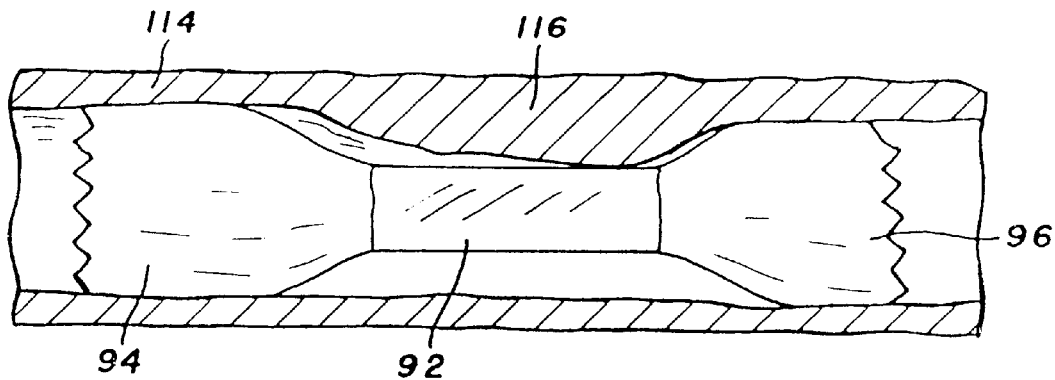
Figure 16:
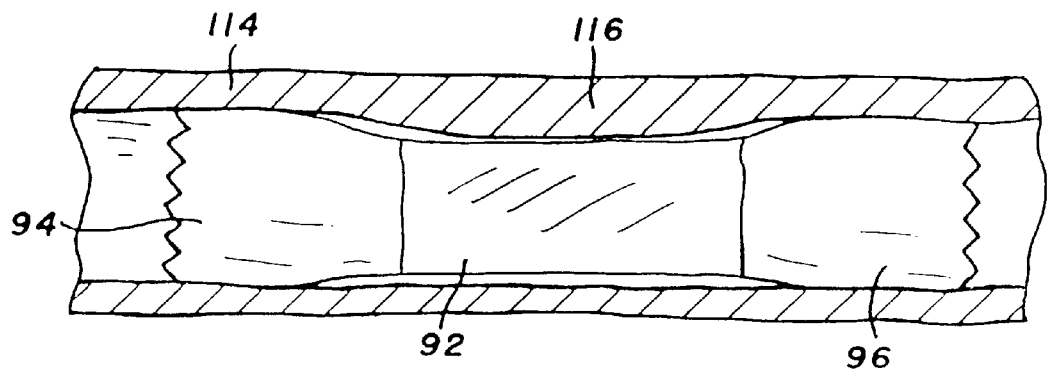
Figure 17:
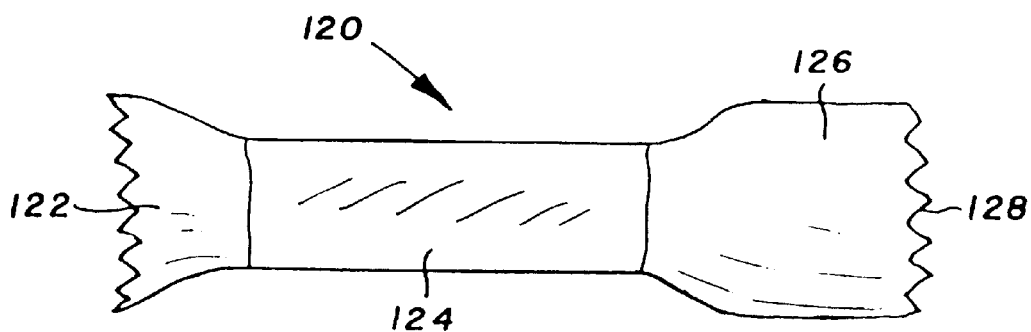

FIG. 15 schematically illustrates the prostheses of FIG. 11 in an esophagus, a short time after its deployment;

FIG. 16 schematically illustrates the prosthesis one day after its deployment; and FIG. 17 illustrates an alternative prostheses constructed according to the present invention, and deployed in an esophagus, with a distal end of the prostheses protruding into the stomach.

DETAILED DESCRIPTION OF THE PREFERRED EMBODIMENTS

Turning now to the drawings, there is shown in FIG. 1 a deployment device 16 for delivering a stent or other prostheses to an intended fixation location within a body cavity, and then controllably releasing the stent for radial self-expansion to a fixation within the body cavity.

The device includes an elongate exterior catheter or tubing 18 constructed of a biocompatible polymer, e.g. polypropylene, FEP or Teflon, with an outside diameter of about 12 mm or less. A central lumen 20 runs the length of catheter 18. On the outside of catheter 18 are visible markings 22 designating cm. When using the device, e.g. in deploying a radially self-expanding prostheses within the esophagus, a physician can determine the extent of insertion into the esophagus based upon these markings. Throughout deployment, the proximal end of exterior catheter 18 remains outside the patient. A hub or handle 24 at the proximal end of the exterior catheter, facilitates manipulation of exterior catheter 18 by hand.

An interior catheter or tubing 26 runs through lumen 20, contained within the exterior catheter. Interior catheter 26 has an outside diameter of approximately 6 mm or less, and is constructed of a biocompatible polymer, e.g. polypropylene, FEP, Hytrel or nylon.

At the distal end of interior catheter 26 is a distal tip 28. The distal tip is flexible, yet sufficiently rigid to be self-supporting rather than pliable when encountering tissue. As a result, distal tip 28 can be used to dilate the esophagus along regions where a tumor or other stricture is present. Over the majority of its length, distal tip 28 has a diameter substantially equal to the interior tubing diameter, with a distal converging end 30 formed as part of the tip.

A proximal region 32 of interior catheter 26 extends proximally beyond hub 24. Visible markings on the outer surface of catheter 26 define three adjacent segments of the proximal region, as indicated at 34, 36 and 38, respectively. These segments can be different colors if desired, to enhance their recognition. These segments, and more particularly the position of hub 24 along them, indicate the axial position of exterior catheter 18 relative to interior catheter 26. The segments further indicate the stages of stent deployment, as is later explained.

At the proximal end of interior catheter 26 is a hub or handle 40, which facilitates manipulation of the interior catheter by hand. A lumen 42 (FIG. 3) runs the length of interior catheter 26, to accommodate a guidewire 44.

FIG. 3 reveals further features of interior catheter 26, including a distal enlargement feature 46 positioned just proximally of tip 28. Enlargement feature 46 is cylindrical, and includes a mid-portion or medial region 48 having an outside diameter of about 11–12 mm, substantially equal to the diameter of lumen 20. Thus the enlargement feature is in surface engagement with exterior catheter 18 as shown in FIG. 3, and can slide relative to the exterior catheter.

Enlargement feature 46 also includes proximal and distal transition regions at 50 and 52, respectively. Distal transition region 52 diverges proximally from the distal tip to the mid-portion of the enlargement feature. The proximal transition region converges proximally from the mid-portion to the interior catheter.

An annular restraining sleeve 54 surrounds a distal region 56 of the interior catheter. The sleeve is formed by wrapping double sided adhesive tape around the interior catheter so that the sleeve adheres to the inner catheter and also exhibits a tackiness over its exterior surface. Radiopaque markers 58, 60, 62 and 64 surround the sleeve. These markers can be surrounded by sleeve 54 if desired.

Surrounding sleeve 54 is a radially self-expanding stent 66. The stent preferably is of open weave or mesh construction, formed of multiple helically wound strands or filaments of a flexible material such as body compatible stainless steel. The durometer of sleeve 54 is substantially less than the durometer of catheters 18 and 26. Retaining sleeve 54 is sized such that whenever exterior catheter 18 radially compresses stent 66, the catheter also is pressing the stent into a surface engagement with the retaining sleeve, to the point of at least slightly elastically deforming the sleeve. As a result, friction between the stent and sleeve 54 substantially exceeds friction between the stent and the interior surface of catheter 18. Given the length and positioning of retaining sleeve 54, stent 66 when compressed contacts the sleeve over its entire axial length. In any event, the stent should contact sleeve 54 over at least its entire medial region. Thus, there is no tendency in the stent to travel with exterior catheter 18 as this catheter moves axially relative to catheter 26. Rather, the stent remains essentially fixed in the axial direction relative to catheter 26. As a result, the axial position of interior catheter 26 serves as a reliable indication of the location of stent 66, not only before deployment, but throughout most of the deployment procedure.

An adhesive layer 68 on the exterior surface of retaining sleeve 54 of course further insures that stent 66 remains axially fixed relative to the interior catheter. It has been found that adhesive is not necessary when deploying a stent of open weave or mesh construction over its entire length. Friction due to the lower durometer of the retaining sleeve, alone, has been found sufficient to anchor the stent. However, when a silicone or other polymeric film covers the stent medial region, the adhesive is a key factor, in combination with the low durometer, in retaining the stent during external catheter withdrawal.

Figure 4:
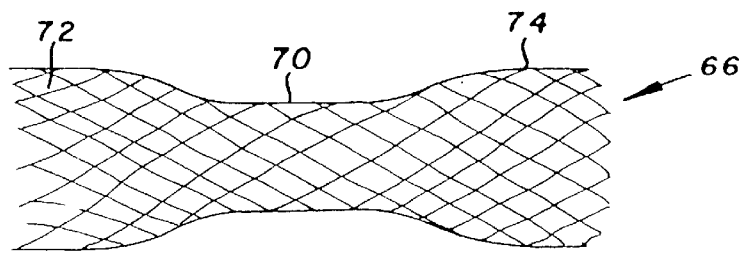
FIG. 4 is a side elevation of the stent in a relaxed configuration.

As shown in FIG. 3, stent 66 is in a reduced-radius and axially elongated configuration. The stent is compressed into this configuration due to the external radial force provided by exterior catheter 18. When the exterior catheter is withdrawn, thus removing the external force, stent 66 assumes a normal or relaxed configuration shown schematically in FIG. 4. More particularly, a medial region 70 of the stent assumes a diameter of about 20 mm, and opposite end regions 72 and 74 of the stent assume a diameter of about 30 mm.

Hub 24 is fixed to exterior catheter 18, and has an opening to accommodate interior catheter 26 such that the interior catheter is slidable axially relative to hub 24. Hub 40 has an opening formed therethrough, to accommodate guidewire 44.

An annular sleeve detent 76 surrounds the proximal region of interior catheter 26, between hubs 24 and 40. When positioned as shown in FIG. 1, retaining sleeve 76 surrounds the interior catheter and abuts the hubs to prevent any substantial movement of the interior catheter axially relative to exterior catheter 18. Sleeve 76 thus functions as a safety detent, preventing premature deployment of the stent. Sleeve detent 76 has a lengthwise slit, and thus is easily removed from proximal region 32 for stent deployment.

Deployment of stent 66 within the esophagus is considered appropriate when a tumor, lesion or other stricture has constricted the esophageal passageway to a diameter less than about 15 mm. This represents a severe constriction in light of the normal passageway diameter of about 22 mm. Deployment begins by oral insertion and positioning of guidewire 44, using an endoscope (not shown) in a manner well known in connection with treating not only the esophagus but other body lumens, e.g. arteries. The guidewire catheter has a diameter of about 0.035–0.042 inches. Once the guidewire has been properly positioned, the endoscope is withdrawn.

Next, deployment device 16, including stent 66 radially compressed as shown in FIG. 3, is inserted over guidewire 44 and thus is directed toward the desired treatment location as it is moved distally. Eventually, distal tip 28 of the device encounters the esophageal stricture. At this point, the deployment device is firmly but carefully moved further in the distal direction, to utilize distal tip 28 to dilate the region of the stricture. Once the distal tip has entered the region, distal transition region 52 and mid-portion 48 of the enlargement feature are used to further dilate the region of the stricture, eventually to the point where the distal region of exterior catheter 18 is passed through the region of the stricture. Thus, according to one feature of the present invention, the stent delivery device also dilates the region of the esophageal stricture and no separate dilating tool is required.

With the distal end of the exterior catheter past the stricture, stent deployment is initiated. More particularly, with interior catheter 26 held substantially fixed, hub 24 is manipulated by hand to withdraw exterior catheter 18 in the proximal direction. When hub 24 encounters segments 34 along the proximal region 32 of the interior catheter, the distal end of the exterior catheter is near the distal end of stent 66, meaning that deployment is about to begin. Before further withdrawal of the exterior catheter, it is advisable to re-examine the stent position, to insure that medial region 70 of the stent is aligned with the stricture, represented in FIG. 5 by a tumor 78 in esophageal wall tissue 80. With stent 66 properly aligned, exterior catheter 18 is withdrawn proximally until hub 24 encounters segment 36. As shown in FIG. 5, by the time the hub encounters segment 36, distal end region 72 of stent 66 is released from the exterior catheter and radially self-expands until it encounters tissue 80.

FIG. 6 illustrates further withdrawal of exterior catheter 66, to the point where hub 24 encounters marked segment 38. This corresponds to release of stent 66 over its distal region and medial region, i.e. roughly two-thirds deployment. One of the advantages of retaining sleeve 54 is that even at this advanced stage, it remains possible to recover or retract stent 66 by moving exterior catheter 18 distally relative to interior catheter 26. Such stent recapture occasionally is necessary, in order to reposition stent 66 relative to the esophageal stricture. More generally, the stent is virtually always retractable, even when a majority of its axial length is released. With the stent retaining means of the present invention, stents have been found to be retractable after up to 80 percent deployment.

FIG. 7 illustrates full withdrawal of exterior catheter 18 to completely release stent 66, corresponding to proximal movement to the point where hub 24 is at the proximal end of proximal segment 38. Stent 66 is radially expanded (and axially shortened) over its entire length, although not expanded to its normal, relaxed configuration. Rather, the stent expands only until the constraining force of esophageal tissue 80 and the remaining residual force in the stent reach an equilibrium. In the equilibrium state, stent 66 has a diameter substantially larger than the diameter of enlargement feature 46, in particular its mid-portion. Accordingly, interior catheter 26 can be withdrawn proximally through the expanded stent. Proximal transition region 50 further insures against the possibility of enlargement feature 46 being caught during attempted withdrawal, either by stent 66 or a stricture in the esophagus. However, as a precaution against this event, the physician can advance exterior tubing 18 distally through the deployed stent until its distal end once again surrounds the enlargement feature as shown in FIG. 1.

FIG. 8 illustrates a proximal withdrawal of enlargement feature 46 and distal tip 28 past stent 66. Withdrawal of the delivery tool is followed by withdrawal of guidewire 44, unless the guidewire is retained for guiding another tool, e.g. an endoscope, into the esophagus.

Figure 9:
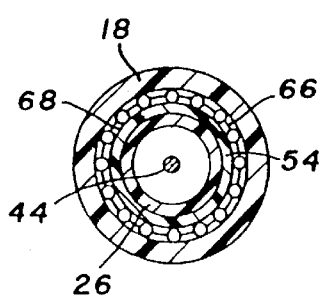
FIG. 9 is a sectional view taken along the line 8—8 in FIG. 3, showing a stent retaining layer.
Figure 10:
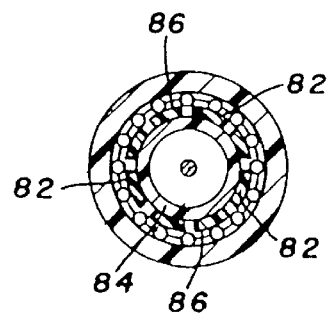
FIG. 10 is a sectional view similar to FIG. 9, but showing an alternative embodiment device utilizing stent retaining strips in lieu of the retaining layer shown in FIG. 9.

FIG. 9 illustrates the radial compression of stent 66 by exterior catheter 18 to press the stent into surface engagement with restraining sleeve 54. FIG. 10 is a view similar to FIG. 9, but showing an alternative deployment device in which several strips 82, elongate in the axial direction, are spaced apart angularly in an array about an interior catheter 84. Like sleeve 54, the strips are constructed of a material having a substantially lower durometer than the catheters. The strips are secured to the interior catheter and, if desired, are provided with adhesive coatings along their radially outward surfaces, as indicated at 86.

While stent 66 is satisfactory in many respects, it is unsuitable for treatment of certain cancerous tissue in the esophagus. Such tissue is not as strong as healthy esophageal tissue, and thus is subject to rupture or other damage from an excessively rapid and forceful expansion of a conventional open weave stent. The stent is subject to tumor ingrowth due to its open weave construction. Further, points or edges at the opposite ends of the stent may perforate the esophageal wall.

A prostheses or stent 90, shown in FIG. 11, is constructed to address all of these concerns. Like stent 66, stent 90 is of mesh or open weave construction, comprised of multiple braided and helically wound strands. Stent 90 has a medial sleeve or region 92, a distal cuff 94 and proximal cuff 96. The proximal and distal ends of the stent are directed radially inward, as indicated at 98 and 100. When stent 90 is in its relaxed or normal configuration as shown in the figure, medial region 92 has a diameter of about 20 mm, and the cuffs have a diameter of about 30 mm. The filaments forming the stent, preferably of a body compatible stainless steel, are about 0.22 mm or less in diameter.

While cuffs 94 and 96 are open, medial region 92 is circumscribed, i.e. completely covered, with a continuous polymeric film, preferably silicone. The silicone film is applied by dip coating of stent 90, in which event the film initially covers one of the cuffs, and is removed from that cuff prior to using the stent. The preferred thickness of the silicone film is in the range of 0.003–0.01 inches (0.075–0.25 mm), and is controlled primarily by the number of dip coating applications. More specifically, from three to five dip coatings result in a thickness within the preferred range.

The silicone film is elastic, and thus is radially self-expanding like the remainder of stent 90. However, the silicone reinforces the medial region such that it has a much greater restoring force than the open weave portions of the stent. In particular, while cuffs 94 and 96 tend to recover virtually instantaneously from a radially compressed configuration, a tumor would inhibit their recovery. Medial region 92 recovers against a tumor, although it has been observed to take 24 hours for recovery. It has been found that the recovery rate of the medial region 92 can be controlled by controlling the thickness of the silicone film.

The gradual recovery rate of the medial region against tumors affords several advantages which make stent 90 particularly well suited for treating esophageal strictures. Certain advantages arise from the coated medial region itself, and other advantages arise from the combination of the medial region with cuffs 94 and 96. Considered alone, medial region 92 provides an effective barrier to tissue ingrowth, because of the continuous silicone film. The gradual recovery of medial sleeve 92, from the radially compressed state when the stent is deployed, substantially reduces the chance that weakened cancerous tissue will be harmed during stent radial self-expansion. While a recovery rate of about one hour would significantly reduce most of the risk, the observed recovery rate of 24 hours is highly preferred. A further advantage arises from the fact that the residual force along the medial region is greater than the residual force along the more rapidly expanding cuffs. As a result, the maximum radial dilating force is provided along that portion of stent 90 aligned with the esophageal stricture.

As mentioned above, cuffs 94 and 96 radially expand rapidly upon their release from a stent confining means such as exterior catheter 18. Thus, the cuffs rapidly contact and reach equilibrium with healthy tissue of the esophageal wall. Residual force in the cuffs at equilibrium is much less than the residual force along medial region 92. As a result, cuffs 94 and 96 readily conform to changes in the esophageal wall during swallowing and other convulsions of the esophagus. Thus, the cuffs are particularly effective in resisting either proximal or distal migration the stent. The open weave construction of the cuffs does not give rise to the problem of tumor ingrowth, since medial region 92 is aligned with the stricture, while the cuffs engage healthy tissue.

Figure 12:
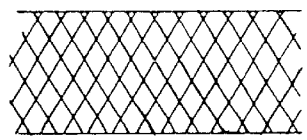
FIGS. 12 and 13 illustrate alternative braid angle configurations for self-expanding prostheses.
Figure 13:
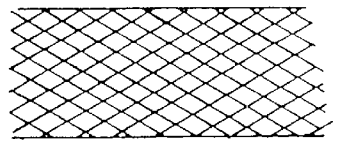

Yet another advantage of the silicone film is that it provides reinforcement along medial region 92, enabling the stent to be constructed with a reduced braid angle. The braid angle is measured, based on the filament incline from the axial dimension of the stent. FIGS. 12 and 13 illustrate a high braid angle and a low braid angle, respectively. In each case, the stent is oriented with its axial length in the horizontal direction. Heretofore, 90 degrees has been considered a lower practical limit for the braid angle of a mesh or open weave stent. Employing the silicone film, however, enables a reduction of the braid angle to as low as 70 degrees, as illustrated in FIG. 13. The advantage of a lower braid angle resides in the fact that the braid angle determines the ratio of stent axial shortening to radial increase, as the stent self-expands. With a reduced braid angle, there is less axial shortening for a given radial expansion. Due to the reduced axial "drift", the stent can be more accurately positioned within body lumens during its deployment.

Figure 14:
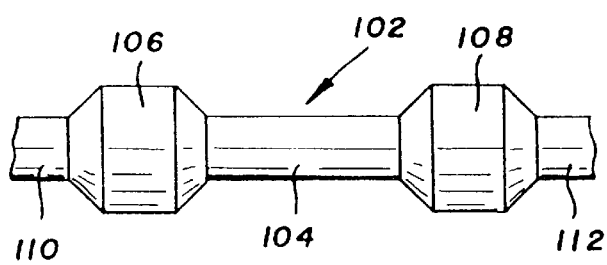
FIG. 14 is a side elevational showing a mandrel used in forming the prosthesis of FIG. 11.

FIG. 14 illustrates a mandrel 102 particularly well suited for forming stent 90. Mandrel 102 includes a central shank 104, enlargements 106 and 108 on opposite sides of the shank, and end portions 110 and 112. To form the stent, the individual filaments or strands are wound in helical fashion to form an open weave cylinder. The cylinder is placed upon mandrel 102 and heated to a temperature in the range of from about 800–1,000 degrees F. The filaments, when cooled, retain the shape of the mandrel. Portions of the stent formed along the outer ends of the mandrel are trimmed, leaving the inwardly directed ends 98 and 100.

FIGS. 15 and 16 schematically illustrate stent 90 after its deployment in the esophagus. An esophageal wall 114 includes a tumor 116. Using a device such as device 16, stent 90 is deployed as above explained. Medial region 92 of the stent is aligned with the tumor, and cuffs 94 and 96 are aligned with healthy portions of the esophageal wall 114 proximally and distally of tumor 116. The cuffs expand into engagement and equilibrium with esophageal wall 114 substantially immediately after deployment. Medial region 92, while it may engage tumor 116, remains radially reduced.

FIG. 16 illustrates stent 90 one day after deployment. Medial region 92 has recovered, and presses against tumor 116 to maintain the esophageal passage along the stricture. The diameter of medial region 92 at equilibrium is likely to be greater than two-thirds of the cuff diameter at equilibrium, because of the greater residual force due to the silicone film.

FIG. 17 illustrates another alternative stent 120 particularly suited for esophageal placement near the stomach, more particularly when a flared distal end or lower end 122 of the stent is near or protruding into the stomach, e.g. to treat a stricture near the stomach. Accordingly, stent 120 includes a distal region 124 circumscribed with a continuous silicone film, and a proximal cuff 126 of mesh or open weave construction. The proximal end 128 of the stent is inclined inward, to avoid the chance for esophageal perforation. Stent 120 can be deployed with a tool substantially identical to deployment device 16.

Thus, in accordance with the present invention, a radially self-expanding stent includes a barrier region circumscribed by a silicone film to reduce tumor ingrowth, in combination with a fixation region of open weave construction. The stent is resistent to migration and to tumor ingrowth, and can be configured to recover gradually along its barrier region after deployment, to minimize harm to weakened, cancerous tissue. The device for deploying the stent incorporates a dilation tip and a further dilation feature proximally of the tip, to eliminate the need for a separate esophageal dilating tool. During delivery and deployment, the stent surrounds and is radially compressed against a low durometer stent restraining sleeve. This fixes the stent axially with respect to an interior catheter of the deployment device, for enhanced accuracy in stent positioning and enhanced ability to recover or retract a partially deployed stent.

What is claimed is:

1. An apparatus for deploying a radially expandable stent within a body lumen, including:

a stent confining device adapted to maintain a radially expandable stent in a delivery configuration in which the radially expandable stent has a reduced radius;

an elongate and flexible stent delivery device having a proximal end, a distal end, and a distal region near the distal end for use in delivering the radially expandable stent into a body lumen and in positioning the stent at a treatment site within the body lumen with the stent surrounding the delivery device along the distal region, while the proximal device along the distal region, while the proximal end of the stent delivery device remains outside of the body;

an axial stent restraining apparatus disposed along the distal region of the delivery device, wherein friction between said restraining apparatus and said stent is greater than friction between said stent confining device and said stent; and a position control apparatus operably associated with the delivery device and the confining device for moving the confining device axially relative to the delivery device toward and away from a confinement position in which the confining device maintains the radially expandable stent in the delivery configuration and urges the stent into a surface engagement with the axial stent restraining apparatus;

wherein the axial stent restraining apparatus, during said surface engagement, tends to maintain the radially expandable stent axially aligned with the deployment device as the confining device is moved axially away from the confinement position to release the stent for radial expansion; and a cylindrically shaped detent device, cut axially for removable mounting to the stent delivery device portion near the proximal end, for preventing any substantial axial movement of the stent delivery device relative to the stent confining device, to maintain the stent confining device in the confinement position.

2. The apparatus of claim 1 wherein:

the stent delivery device comprises a first elongate and flexible length of tubing.

3. The apparatus of claim 2 further including:

a central lumen running the axial length of the first tubing, for accommodating a guidewire.

4. The apparatus of claim 2 further including:

a distal tip at the distal end of the first tubing, for dilating a malignant stricture at the treatment site.

5. The apparatus of claim 2 wherein:

the stent confining device comprises a second elongate and flexible length of tubing having a lumen running the length thereof, and wherein the first length of tubing is contained within the lumen with a proximal portion of the first tubing extended proximally of the second tubing when the second tubing is in the confinement position.

6. The apparatus of claim 5 wherein:

the position control apparatus comprises a first hub at the proximal end of the first tubing and a second hub at the proximal end of the second tubing.

7. The apparatus of claim 5 wherein:

the axial restraining apparatus comprises a sleeve surrounding the first tubing along the distal region.

8. The apparatus of claim 7 further including:

an adhesive applied to an exterior surface of the sleeve.

9. The apparatus of claim 5 wherein:

the axial stent restraining apparatus comprises a plurality of elongate strips disposed along the distal region.

10. The apparatus of claim 9 wherein:

the strips are oriented axially and spaced apart angularly from one another to form a set of the strips surrounding the first tubing.

11. The apparatus of claim 10 further including:

an adhesive layer along a radially outward surface of each of the strips.

12. The apparatus of claim 5 further including:

visible indicia along the proximal portion of the first tubing for indicating the position of a distal end of the second tubing with respect to the distal region of the first tubing.

13. The apparatus of claim 12 wherein:

said indicia further measure the extent to which the radially self-expanding stent is deployed.

14. The apparatus of claim 5 further including:

visible markings along at least a proximal region of the second tubing for indicating the extent of insertion of the second tubing into the body lumen.

15. The apparatus of claim 5 further including:

an enlargement feature near the distal end of the stent delivery device, said enlargement feature having a diameter substantially equal to an interior diameter of the second tubing, a distal transition region diverging proximally from the tip to a mid-portion of the enlargement feature, and a proximal transition region converging in the proximal direction from the enlargement feature mid-portion.

16. The apparatus of claim 2 further including:

radiopaque markings on the first tubing along the distal end region.

* * * * *